(12) United States Patent
Kursikowski et al.

(10) Patent No.: US 10,082,476 B2
(45) Date of Patent: Sep. 25, 2018

(54) SENSING OF MEDIA ITEMS

(71) Applicant: NCR Corporation, Duluth, GA (US)

(72) Inventors: Derek Kursikowski, Kitchener (CA);
Fredrik L. N. Kallin, Waterloo (CA);
Daniel Choi, Waterloo (CA)

(73) Assignee: NCR Corporation, Atlanta, GA (US)

( * ) Notice: Subject to any disclaimer, the term of this patent is extended or adjusted under 35 U.S.C. 154(b) by 14 days.

(21) Appl. No.: 14/136,735

(22) Filed: Dec. 20, 2013

(65) Prior Publication Data

US 2015/0177170 A1 Jun. 25, 2015

(51) Int. Cl.
*G01N 27/04* (2006.01)
*G01N 33/34* (2006.01)

(52) U.S. Cl.
CPC .......... *G01N 27/048* (2013.01); *G01N 33/34* (2013.01)

(58) Field of Classification Search
CPC ... G01N 27/048; G01N 27/223; G01N 27/121
USPC ....................................... 324/694
See application file for complete search history.

(56) References Cited

U.S. PATENT DOCUMENTS

| | | | | |
|---|---|---|---|---|
| 4,522,060 A | * | 6/1985 | Murata et al. | 73/335.03 |
| 4,532,469 A | * | 7/1985 | Wardell | 324/689 |
| 5,720,376 A | * | 2/1998 | Polidoro | G07F 7/04 |
| | | | | 194/207 |
| 7,088,115 B1 | * | 8/2006 | Glenn et al. | 324/691 |
| 7,489,141 B1 | * | 2/2009 | Vermeire et al. | 324/646 |
| 2002/0003163 A1 | * | 1/2002 | Peebles et al. | 235/379 |
| 2008/0211521 A1 | * | 9/2008 | Lock | 324/696 |
| 2009/0164156 A1 | * | 6/2009 | Colston et al. | 702/65 |
| 2011/0064424 A1 | * | 3/2011 | Knausdorf et al. | 399/16 |
| 2014/0253150 A1 | * | 9/2014 | Menzel et al. | 324/664 |

\* cited by examiner

*Primary Examiner* — Son Le
*Assistant Examiner* — Akm Zakaria
(74) *Attorney, Agent, or Firm* — Schwegman, Lundberg & Woessner (57) ABSTRACT

The present invention provides a method and apparatus for determining at least one parameter associated with at least one media item, further comprising a first electrical contact element and a further electrical contact element supported in a spaced apart relationship via a contact support, wherein at least one electrical characteristic associated with a pathway between the first and further electrical contact elements is indicative of at least one parameter of at least one media item in contact with and extending between the first and further electrical contact elements.

22 Claims, 5 Drawing Sheets

SENSING OF MEDIA ITEMS

FIELD OF THE INVENTION

The present invention relates to the sensing of media items. In particular, but not exclusively, the present invention relates to sensing at least one media item, such as a banknote, deposited at a Self-Service Terminal (SST) and determining a parameter associated with the media item, such as a moisture content of the media item.

Various situations are known in which media items are transported along different transport pathways in an SST. In a known SST, such as a bank note depositing Automated Teller Machine (ATM), an ATM customer is allowed to deposit one or more banknotes (without having to place a banknote in a deposit envelope) in a publicly accessible, unattended environment. To deposit a banknote, the ATM customer inserts an identification card through a card slot at the ATM, enters a total value of banknotes being deposited, and then inserts the banknote(s) to be deposited through a deposit slot of a banknote acceptor. The transport mechanism receives the banknote and transports the banknote in a forward direction along an in-feed transport path to a number of locations within the ATM to process the banknote for crediting the customer's account accordingly. Other items of media include cheques, vouchers, coupons, giros, or the like.

It is known for a criminal to attempt to deposit wet banknotes of nominal value at the ATM in order to cause a jam within the ATM. The jam would then be reported by the criminal claiming that a deposit, of a falsified larger amount, typically in the region of around $300 to $500, was made at the ATM but was never credited into the criminal's account. Once the falsified amount was credited to the account, prior to the jam being confirmed by an authorised person, the amount would be withdrawn by the criminal and the account closed or reported as stolen by the authorised account holder.

SUMMARY OF THE INVENTION

It is an aim of certain embodiments of the present invention to at least partly mitigate the above-mentioned problems.

It is an aim of certain embodiments of the present invention to provide a method and apparatus for determining a parameter associated with at least one media item for SST protection.

It is an aim of certain embodiments of the present invention to provide a method and apparatus for determining a moisture content of at least one media item being deposited at an SST.

It is an aim of certain embodiments of the present invention to provide a method and apparatus for detecting and rejecting wet media items deposited at an ATM to prevent media jams occurring in the ATM for security and antifraud purposes.

It is an aim of certain embodiments of the present invention to provide an apparatus which is simple, inexpensive to manufacture and which may be easily installed in an existing SST.

It is an aim of certain embodiments of the present invention to provide a method and apparatus which reduces the number of failures of an SST, reduces the costs associated with servicing an SST and also increases the marketability of media item processing modules for an SST.

According to a first aspect of the present invention there is provided apparatus for determining at least one parameter associated with at least one media item, further comprising:
a first electrical contact element and a further electrical contact element supported in a spaced apart relationship via a contact support; wherein
at least one electrical characteristic associated with a pathway between the first and further electrical contact elements is indicative of at least one parameter of at least one media item in contact with and extending between the first and further electrical contact elements.

Aptly, the at least one parameter comprises a moisture content of the at least one media item.

Aptly, the at least one electrical characteristic comprises electrical resistance.

Aptly, the apparatus further comprises a processor configured to determine the electrical resistance of at least one media item extending between the first and further electrical contact elements.

Aptly, the processor is configured to determine a change of the electrical resistance relative to a predetermined threshold resistance.

Aptly, the apparatus further comprises an electrical circuit comprising at least one resistor of known resistance connected in series with the first and further electrical contact elements.

Aptly, the processor is configured to measure an output voltage of the electrical circuit to determine the electrical resistance of the at least one media item responsive to a known input voltage of the electrical circuit and the known resistance of the at least one resistor.

Aptly, the electrical circuit further comprises a unity-gain buffer.

Aptly, the electrical circuit further comprises a power source.

Aptly, one or more of the electrical circuit and processor is mounted to the contact support.

Aptly, the first and further electrical contact elements are locatable on a first side of the at least one media item to determine the electrical resistance across or along the at least one media item.

Aptly, the first electrical contact element is locatable on a first face of the at least one media item and the further electrical contact element is locatable on a further face of the at least one media item to measure the electrical resistance through the at least one media item.

Aptly, the pathway between the first and further electrical contact elements is arranged substantially in parallel with a direction of travel of the media item.

Aptly, at least a contact portion of each electrical contact element for contacting the at least one media item is substantially curved in the direction of travel of the media item.

Aptly, the first and further electrical contact elements each comprise a roller.

Aptly, the first and further electrical contact elements are fixed in a direction substantially parallel to a direction of travel of the media item.

Aptly, the first and further electrical contact elements are biased towards the at least one media item.

According to a second aspect of the present invention there is provided a media item processing module comprising apparatus according to the first aspect of the present invention.

According to a third aspect of the present invention there is provided a method of determining at least one parameter associated with at least one media item, comprising:

determining at least one electrical characteristic associated with a pathway between a first electrical contact element and a further electrical contact element supported in a spaced apart relationship via a contact support; wherein the at least one electrical characteristic is indicative of at least one parameter of at least one media item in contact with and extending between the first and further electrical contact elements.

Aptly, the method further comprises:

determining an electrical resistance of the media item extending between the first and further contact elements, wherein the electrical resistance is indicative of a moisture content of the media item.

Aptly, the method further comprises:

monitoring a change of the electrical resistance relative to a predetermined threshold resistance.

Aptly, the method further comprises:

preventing the at least one media item further advancing along a transport path of a media item processing module responsive to the electrical resistance exceeding the predetermined threshold resistance.

Aptly, the method further comprises:

locating the first and further electrical contact elements on a first side of the at least one media item to measure the electrical resistance across or along the at least one media item.

Aptly, the method further comprises:

locating the first electrical contact element on a first face of the at least one media item and locating the further electrical contact element on a further face of the at least one media item to measure the electrical resistance through the at least one media item.

According to a fourth aspect of the present invention there is provided a method of determining at least one parameter associated with at least one media item, comprising:

determining at least one parameter associated with at least one media item when the at least one media item contacts and extends between at least two spaced apart electrical contact elements.

Certain embodiments of the present invention may provide apparatus for detecting moisture in a media item which is easily retrofittable to an existing SST.

Certain embodiments of the present invention may provide the ability to detect and reject wet media items at an SST for security and/or anti-fraud purposes.

Certain embodiments of the present invention may provide apparatus for detecting wet media items being deposited at an SST which requires minimal product and maintenance costs in view of a simple operating concept and few components and which reduces SST servicing downtime and associated servicing costs.

BRIEF DESCRIPTION OF DRAWINGS

Embodiments of the present invention will now be described hereinafter, by way of example only, with reference to the accompanying drawings in which.

DESCRIPTION OF EMBODIMENTS

In the drawings like reference numerals refer to like parts.

Figure 1:
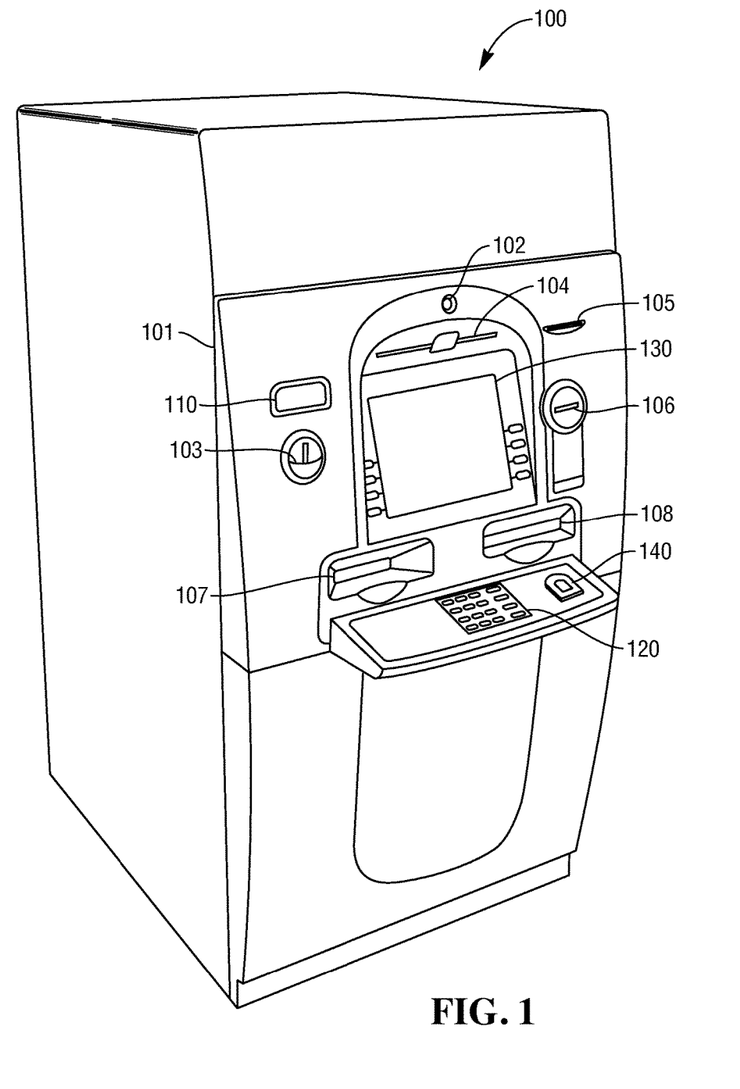
FIG. 1 illustrates a schematic diagram of an ATM according to certain embodiments of the present invention.

FIG. 1 illustrates a self-service cheque depositing terminal in the form of an image-based banknote depositing Automated Teller Machine (ATM) 100. It will be appreciated that certain embodiments of the present invention are applicable to a wide variety of terminals in which items of media such as cheques and/or banknotes and/or giros and/or lottery tickets and/or other such flexible sheet-like items of media are to be transported and directed in different directions. The type of terminal will of course be appropriate for the type of media items being transported.

As illustrated in FIG. 1, the ATM 100 includes a fascia 101 coupled to a chassis (not shown). The fascia 101 defines an aperture 102 through which a camera (not shown) images a customer of the ATM 100. The fascia 101 also defines a number of slots for receiving and dispensing banknotes and a tray 103 into which coins can be dispensed. The slots include a statement output slot 104, a receipt slot 105, a card reader slot 106, a cash slot 107, a further cash slot 108 and a banknote input/output slot 110. The slots and tray are arranged such that the slots and tray align with corresponding ATM modules mounted within the chassis of the ATM.

The fascia 101 provides a customer interface for allowing an ATM customer to execute a transaction. The fascia 101 includes an encrypting keyboard 120 for allowing an ATM customer to enter transaction details. A display 130 is provided for presenting screens to an ATM customer. A fingerprint reader 140 is provided for reading a fingerprint of an ATM customer to identify the ATM customer.

Within the chassis of the ATM it will be understood that items of media, such as banknotes, must be transported from time to time from one location to another. The pathway taken by any particular item of media is dependent upon an operation being carried out at the ATM and may also be dependent upon other factors such as whether a customer of the ATM is authorised and/or whether an item of media being transported satisfies certain pre-determined criteria.

Figure 2:
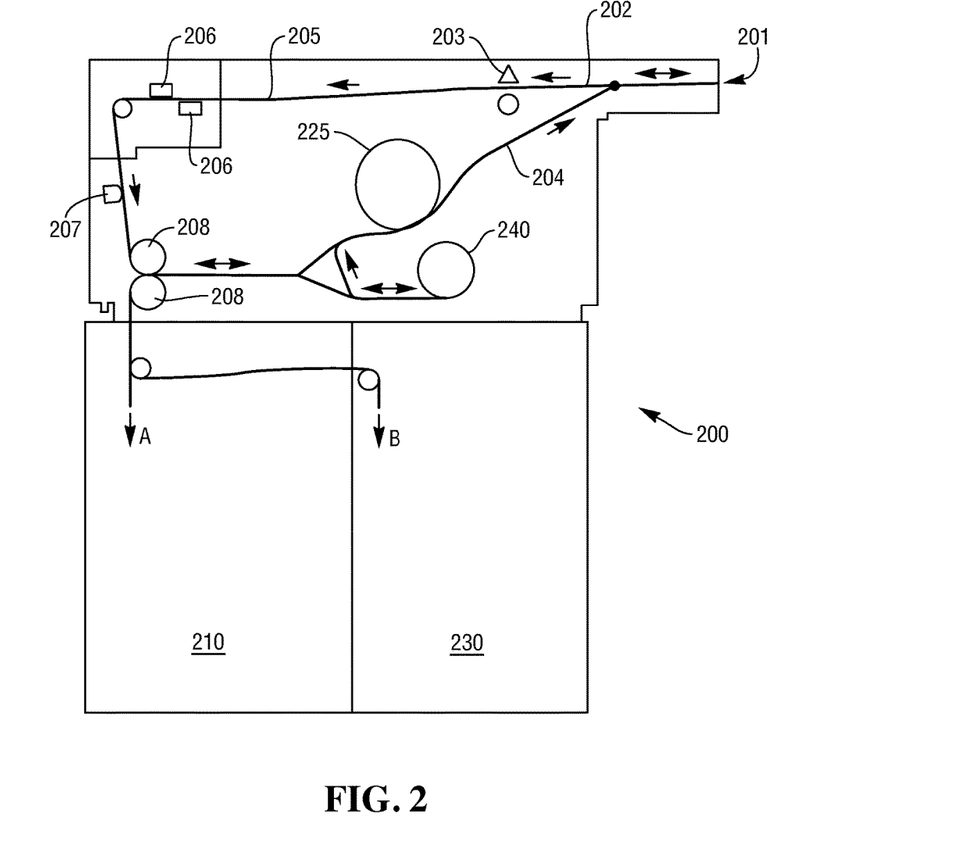
FIG. 2 illustrates a transport pathway within a media item processing module of the ATM of FIG. 1.

FIG. 2 illustrates possible transport pathways and internal modules within the ATM which can be utilised to process deposited banknotes. A banknote processing module 200 has an access mouth 201 through which incoming banknotes are deposited or outgoing banknotes are dispensed. This mouth 201 is aligned with an in-feed aperture in the ATM which thus provides an input/output slot 110. A bunch of one or more media items, such as banknotes, is input or output. Aptly, a bunch of up to a hundred items or more can be received/dispensed. Incoming banknotes follow a first transport path 202 away from the mouth 201 in a substantially horizontal direction from right to left shown in FIG. 2. The first transport path 202 is also referred to as the 'in-feed' path. The banknotes then pass through a feeder/separator 203 and along another pathway portion 205 which is also substantially horizontal and right to left. The banknotes are then de-skewed and read by imaging cameras 206 and an MICR reader 207. Banknotes are then directed substantially vertically downwards to a point between two nip rollers 208. These nip rollers co-operate and are rotated in opposite directions with respect to each other to either draw deposited banknotes inwards (and urge those banknotes towards the right hand side in FIG. 2), or during another mode of operation, the rollers can be rotated in an opposite fashion to direct processed banknotes downwards in the direction shown by arrow A in FIG. 2 into a bin 210. Incoming banknotes which are moved by the nip rollers 208 towards the right can either be diverted upwards (in FIG. 2) into a re-buncher unit 225, or downwards in the direction of arrow B in FIG. 2 into a cash bin 230, or to the right hand side shown in FIG. 2 into an escrow 240. Banknotes from the escrow can be directed to the re-buncher 225 or downwards into the cash bin 230. Banknotes can be reprocessed or returned to a customer via a further transport path 204, also known as the 'return' path.

Figure 3:
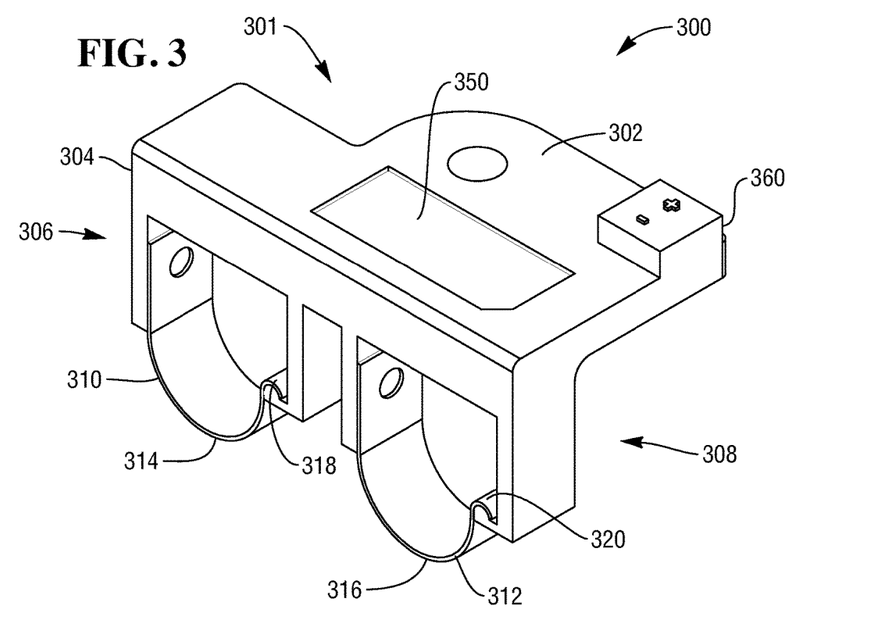
FIG. 3 illustrates an embodiment of the present invention in which the electrical contact elements are fixed with respect to the contact support.

As illustrated in FIG. 3, a sensing apparatus 300 according to certain embodiments of the present invention includes a support member 301 having an attachment portion 302, for attaching the apparatus 300 to a chassis of a media item processing module 200 proximal to the in-feed transport path, and a support portion 304 extending substantially perpendicularly downwardly from the attachment portion 302. A suitable location within the media item processing module 200 for the apparatus to be located is upstream of the feeder/separator 203 but other suitable locations can be envisaged.

The support portion 304 includes two pairs of spaced apart elongate members 306, 308 wherein each elongate member of each pair has a free end distal from the attachment portion 302. Each pair of spaced apart elongate members 306, 308 supports a respective electrical contact element 310, 312. Each electrical contact element 310, 312 is formed from a curved strip of electrically conductive material, such as copper. Each contact element is curved to prevent snagging with or damage to a media item traveling thereunder and in contact therewith. Each element 310, 312 is fixed at a first end thereof to a respective one of a corresponding pair of the elongate members 306, 308 and is coupled at a second end to a remaining one of the corresponding pair of elongate members 306, 308. Each contact element is formed to act as a leaf spring and bias a respective contact portion 314, 316 towards a media item to be sensed to apply a compression force to the media item to ensure a positive contact with the media item is achieved for effective sensing thereof. The second end 318, 320 of each contact element 310, 312 is free to move upwardly with respect to the elongate member to which it is coupled to provide an amount of flexibility and resilience to each contact element to prevent one or more media items being damaged when moved along a transport path of the media item processing module and into contact with the contact elements.

As shown in FIG. 3, the electrical contact elements 310, 312 may be arranged substantially in-line and parallel with a direction of travel of the media item along a transport path of the media item processing module 200. Alternatively, the electrical contact elements 310, 312 may be arranged across a media item, i.e. arranged substantially perpendicular to the direction of travel of a media item. Further alternatively, the electrical contact elements 310, 312 may be arranged substantially diagonally across a media item to be sensed. It will be envisaged that any desired arrangement of the electrical contact elements according to certain embodiments of the present invention may be suitable.

Figure 4:
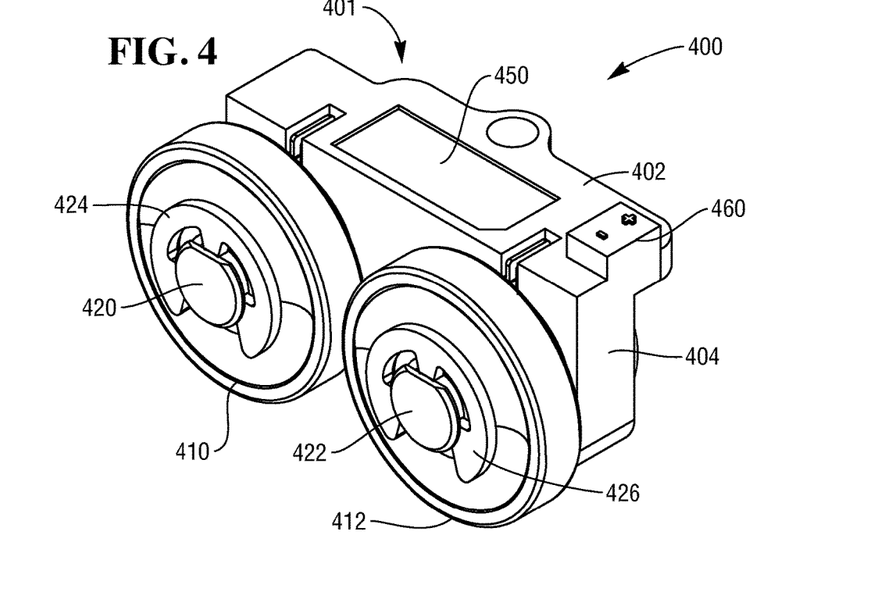
FIG. 4 illustrates an embodiment of the present invention in which the electrical contact elements are rollers for locating on a first face of the media item or for locating on different faces of a media item.
Figure 5:
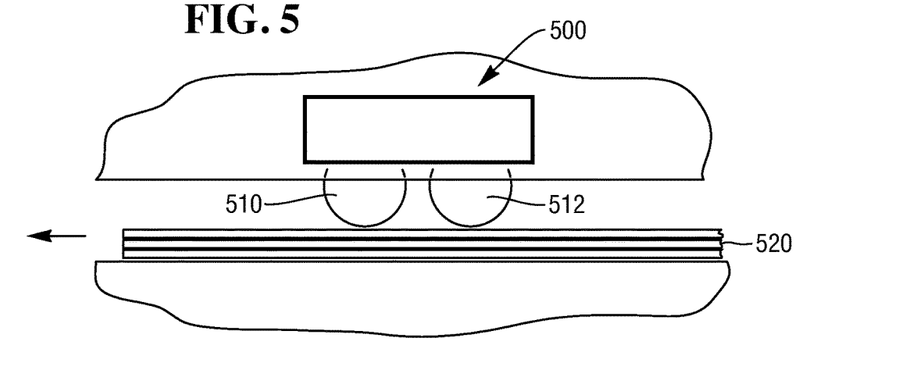
FIG. 5 illustrates an embodiment of the present invention in which the electrical contact elements are located on a first face of a bunch of media items.
Figure 6:
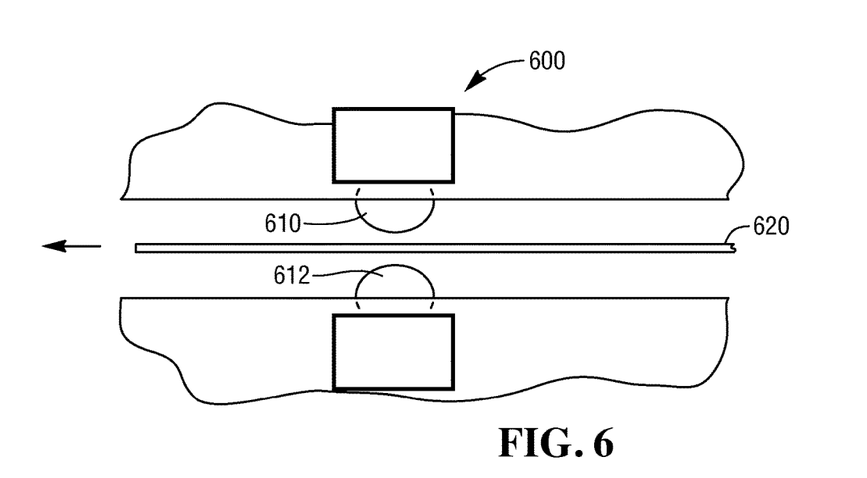
FIG. 6 illustrates an embodiment of the present invention in which the electrical contact elements are located on different faces of a media item.

As shown in FIG. 4, the electrical contact elements 410, 412 of an alternative sensing apparatus 401 include a first roller 410 spaced apart from a second roller 412. Each roller is rotationally mounted to the support member 400 via a respective shaft 420, 422 to rotate with a media item travelling below and in contact with each roller. Each roller is attached to a respective shaft 420, 422 by a respective circlip 424, 426. As shown in FIG. 5, the apparatus 500 may be arranged such that both rollers are located to contact and roll with an upper face a media item 520 being transported below the rollers. Alternatively, as shown in FIG. 6, the apparatus 600 may be arranged to contact and roll with different faces of the media item 620 such that at least one media item is received between the rollers. Each roller is biased by a respective spring (not shown) towards the media item to thereby provide a compression force on the media item to ensure positive contact and effective sensing thereof.

Further alternatively, a combination of fixed and rotatable contact elements can be envisaged.

Figure 7:
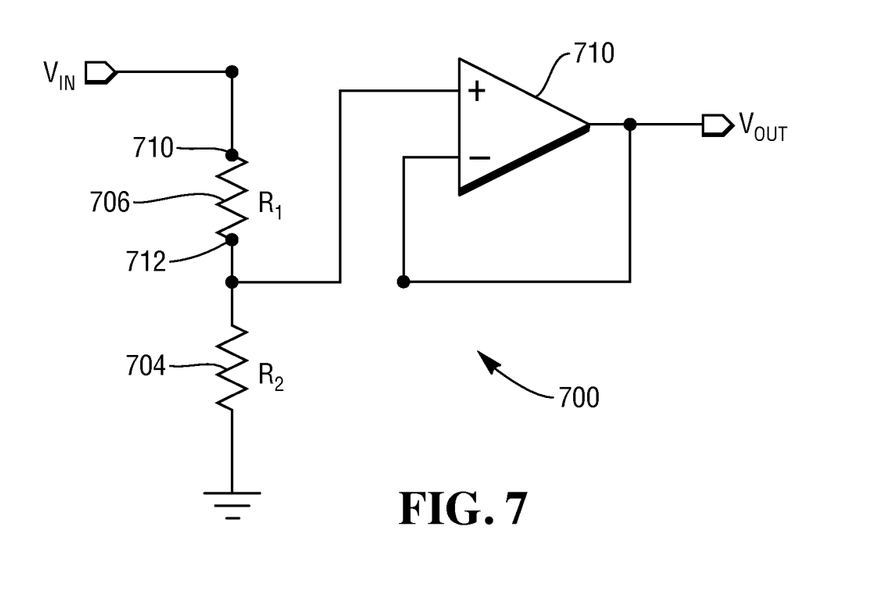
FIG. 7 illustrates a circuit diagram of the electrical circuit of the apparatus according to certain embodiments of the present invention.

As shown in FIGS. 3 and 4, the sensing apparatus 301, 401 further includes an electrical circuit 350, 450 which is mounted to the support member 302, 402 and connected to each contact element. As shown in FIG. 7, the electrical circuit 700 includes a resister 704 of known resistance $R_2$ and a unity-gain buffer 702 connected to the electrical contact elements 710, 712 and a power source (not shown). The power source may be a power source utilised by the ATM for general operation thereof and connected via suitable terminals 360, 460 (as shown in FIGS. 3 and 4) to the sensing apparatus 300, 400 or may be a separate power source mounted to the respective support member 302, 402. The contact elements 710, 712 are connected in series with the known resistor 704 to provide a voltage divider circuit 700. The unity-gain buffer 702 is present so that the electrical circuit draws relatively little current from the power source and so that the power of the circuit is disturbed very little. When a circuit has a relatively high impedance, relatively little current is drawn from the circuit. Thus, in view of Ohm's Law (I=V/R), the greater the resistance of the circuit, the less current is drawn from a power source connected to the circuit. Thus, the power of the circuit is not affected when current is feeding a high impedance load. Of course, other suitable electrical circuits can be envisaged.

In use, when a media item 706 is in contact with and extends between the contact elements 710, 712, the electrical circuit 700 is complete and an electrical current is passed through the media item. The media item 706 acts as a second resistor of resistance $R_1$ connected in series with the resistor 704 of known resistance $R_2$. The resistance of the media item is variable in that a change to the material, composition, structure and/or state of the media item will affect its electrical resistance. For example, a dry media item containing substantially no moisture will have an electrical resistance $R_{1dry}$. However, when the media item becomes wet, the media item will become more electrically conductive and its resistance $R_1$ will decrease to $R_{1wet}$, wherein $R_{1wet}$ is less than $R_{1dry}$.

A processor (not shown) of the ATM is connectable with the electrical circuit 700 and is configured to monitor an output voltage $V_{out}$ of the circuit relative to a known input voltage $V_{in}$ and to determine an electrical characteristic associated with a pathway between the first and second electrical contact elements. As described above, one characteristic is electrical resistance of the media item. Other characteristics include capacitance, impedance, electrical conductivity, or the like.

To determine the electrical resistance of the media item in contact with and extending between the electrical contact elements 710, 712, the following equation is used:

$$V_{out} = \frac{R_2}{R_1 + R_2} \cdot V_{in}$$

such that:

$$R_1 = \frac{R_2 \cdot V_{in}}{V_{out}} - R_2$$

wherein:
$V_{out}$ is output voltage;
$V_{in}$ is input voltage;
$R_1$ is the sensed resistance of the media item 706; and
$R_2$ is the known resistance of the resistor 704.

The processor is configured to determine a change in the electrical resistance $R_2$ of the media item 706 relative to a predetermined threshold electrical resistance. The predetermined electrical resistance may be a known electrical resistance of a dry or genuine media item, for example, or may be a preselected electrical resistance which may correspond to a normal state of a media item in normal operating conditions, such as an expected moisture content of the media item in normal conditions. When the sensed electrical resistance falls below the predetermined electrical resistance, such as when the media item is wet, the processor will determine this change and perform an action responsive to the moisture detection. Such an action may be to stop the media item from further travelling along a transport path within the media item processing module or to reject the media item by returning it along a return path of the media item processing module back to the customer or criminal or into a purge bin of the processing module. As a result, the wet media item is prevented from further entering the transport system of the ATM and the risk of media jams is thus eliminated.

The apparatus according to certain embodiments of the present invention provides for the detection and rejection of wet media items to prevent media item jams within an SST and fraudulent activity at the SST. The apparatus according to certain embodiments of the present invention can be easily retrofitted to an existing SST. The apparatus according to certain embodiments of the present invention may reduce the servicing required at the SST and also increase the marketability of SSTs including the apparatus according to certain embodiments of the present invention.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. Apparatus for determining at least one parameter associated with at least one media item, further comprising:
 a support member mounted along a transport path and including two pairs of non-electrically conductive spaced-apart elongate members;
 a first electrical contact element affixed to a first pair of the spaced-apart elongate members and a further electrical contact element affixed in a spaced apart relationship to a second pair of the spaced-apart elongate members, each electrical contact element including a contact portion for engaging the at least one banknote on the transport path and each electrical contact element formed to act as a leaf spring to bias the at least one banknote against the transport path and apply a compression force to the at least one banknote to ensure a positive electrical contact by the contact portion with the at least one banknote for sensing thereof, and each electrical contact element being curved and adapted to prevent snagging of the at least one banknote as the at least one banknote passes against the electrical contact elements;
 wherein at least one electrical characteristic associated with a pathway between the first and further electrical contact elements is indicative of at least one parameter of at least one banknote in contact with and extending between the first and further electrical contact elements.

2. The apparatus as claimed in claim 1, wherein the at least one parameter comprises a moisture content of the at least one banknote.

3. The apparatus as claimed in claim 1, wherein the at least one electrical characteristic comprises electrical resistance.

4. The apparatus as claimed in claim 3, further comprising a processor configured to determine the electrical resistance of at least one banknote extending between the first and further electrical contact elements.

5. The apparatus as claimed in claim 4, wherein the processor is configured to determine a change of the electrical resistance relative to a predetermined threshold resistance.

6. The apparatus as claimed in claim 4, further comprising an electrical circuit comprising at least one resistor of known resistance connected in series with the first and the further electrical contact elements.

7. The apparatus as claimed in claim 6, wherein the processor is configured to measure an output voltage of the electrical circuit to determine the electrical resistance of the at least one banknote responsive to a known input voltage of the electrical circuit and the known resistance of the at least one resistor.

8. The apparatus as claimed in claim 6, wherein the electrical circuit further comprises a unity-gain buffer.

9. The apparatus as claimed in claim 6, wherein the electrical circuit further comprises a power source.

10. The apparatus as claimed in claim 6, wherein one or more of the electrical circuit and processor is mounted to the contact support.

11. The apparatus as claimed in claim 3, wherein the first and the further electrical contact elements are locatable on a first side of the at least one banknote to determine the electrical resistance across or along the at least one banknote.

12. The apparatus as claimed in claim 3, wherein the first electrical contact element is locatable on a first face of the at least one banknote and the further electrical contact element is locatable on a further face of the at least one banknote to measure the electrical resistance through the at least one banknote.

13. The apparatus as claimed in claim 1, wherein the pathway between the first and further electrical contact elements is arranged substantially in parallel with a direction of travel of the at least one banknote.

14. The apparatus as claimed in claim 13, wherein at least a contact portion of each electrical contact element for contacting the at least one banknote is substantially curved in the direction of travel of the at least one banknote.

15. The apparatus as claimed in claim 1, wherein the first and the further electrical contact elements each comprise a roller.

16. The apparatus as claimed in claim 1 wherein the first and the further electrical contact elements are fixed in a direction substantially parallel to a direction of travel of the at least one banknote.

17. The apparatus as claimed in claim 1, wherein the first and the further electrical contact elements are biased towards the at least one banknote.

18. A banknote processing module comprising apparatus as claimed in claim 1.

19. A method of determining at least one parameter associated with at least one banknote, comprising:
  determining at least one electrical characteristic associated with a pathway between a first electrical contact element and a further electrical contact element supported in a spaced apart relationship via a non-electrically conductive contact support, wherein determining further includes applying a compressive force by each electrical contact to the at least one banknote located between the first electrical contact element and the pathway and between the further electrical contact and the pathway with each electrical contact acting as a leaf spring biasing the at least one banknote against the pathway ensuring a positive electrical contact with the at least one banknote for sensing thereof and each electrical contact being curved and adapted to prevent snagging of the at least one banknote passes against the electrical contact elements;
  wherein the at least one electrical characteristic is indicative of at least one parameter of at least one banknote in contact with and extending between the first and the further electrical contact elements.

20. A method of determining at least one parameter associated with at least one banknote, comprising:
  determining at least one parameter associated with at least one banknote when the at least one banknote contacts and extends between a first electrical contact element and a transport path and between a second electrical contact element and the transport path, the first and second electrical contact elements being spaced apart and each of the first and second electrical contact elements being held between first and second pairs of non-electrically conductive supports, and being generally U-shaped to minimize surface area contact with the at least one banknote to prevent snagging of the at least one banknote as the at least one banknote passes against the electrical contact elements.

21. Apparatus for determining at least one parameter associated with at least one media item, further comprising:
  a first electrical contact element and a further electrical contact element supported in a spaced apart relationship via a contact support, each electrical contact element affixed to an elongated member and each electrical contact element formed to act as a leaf spring to bias a contact portion of each electrical contact element towards the at least one banknote and apply a compression force to the at least one banknote to ensure a positive contact with the at least one banknote for sensing thereof, and each electrical contact element being curved and adapted to prevent snagging of the at least one banknote as the at least one banknote travels past the electrical contacts;
  wherein electrical resistance between the first and further electrical contact elements is indicative of at least one parameter of at least one banknote in contact with and extending between the first and further electrical contact elements;
  an electrical circuit comprising at least one resistor of known resistance connected in series with the first and the further electrical contact elements; and
  a processor configured to determine the electrical resistance of at least one banknote extending between the first and further electrical contact elements, to determine a change of the electrical resistance relative to a predetermined threshold resistance, and to measure an output voltage of the electrical circuit to determine the electrical resistance of the at least one banknote responsive to a known input voltage of the electrical circuit and the known resistance of the at least one resistor.

22. Apparatus for determining at least one parameter associated with at least one media item, further comprising:
  a support member including two pairs of spaced-apart elongate members mounted along a transport path;
  a first electrical contact element affixed to a first pair of the spaced-apart elongate members and a further electrical contact element affixed in a spaced apart relationship to a second pair of the spaced-apart elongate members, each electrical contact element including a contact portion for engaging the at least one banknote on the transport path and each electrical contact element formed to act as a leaf spring to bias the at least one banknote against the transport path and apply a compression force to the at least one banknote to ensure a positive electrical contact by the contact portion with the at least one banknote for sensing thereof, and each electrical contact element being curved adapted to prevent snagging of the at least one banknote as the at least one banknote passes against the electrical contact elements;
  wherein electrical resistance between the first and further electrical contact elements is indicative of at least one parameter of at least one banknote in contact with and extending between the first and further electrical contact elements;

an electrical circuit comprising at least one resistor of known resistance connected in series with the first and the further electrical contact elements; and a processor configured to determine the electrical resistance of at least one banknote extending between the first and further electrical contact elements, to determine a change of the electrical resistance relative to a predetermined threshold resistance, and to measure an output voltage of the electrical circuit to determine the electrical resistance of the at least one banknote responsive to a known input voltage of the electrical circuit and the known resistance of the at least one resistor.

* * * * *